United States Patent [19]

Nadelson

[11] 4,035,427

[45] July 12, 1977

[54] α-T-BUTYL-P-XYLENE-α-α'-DIOLS AND HYPOLIPIDEMIC COMPOSITIONS CONTAINING SAME

[75] Inventor: Jeffrey Nadelson, Lake Parsippany, N.J.

[73] Assignee: Sandoz, Inc., E. Hanover, N.J.

[21] Appl. No.: 607,457

[22] Filed: Aug. 25, 1975

[51] Int. Cl.$^2$ ............... C07C 33/06; C07C 33/10; A61K 31/045
[52] U.S. Cl. ............. 260/618 R; 260/488 CD; 260/592; 260/618 D; 260/618 H; 424/343
[58] Field of Search ............... 260/618 R, 618 D; 424/343

[56] References Cited

U.S. PATENT DOCUMENTS

| | | | |
|---|---|---|---|
| 2,965,622 | 12/1960 | Pannell | 260/618 R |
| 2,967,854 | 1/1961 | Bungs | 260/618 R |
| 3,267,145 | 8/1966 | Lund et al. | 260/618 R |
| 3,867,465 | 2/1975 | Houlihan et al. | 260/618 R |
| 3,879,191 | 4/1975 | Lavanish | 260/618 R |

*Primary Examiner*—Norman Morgenstern
*Attorney, Agent, or Firm*—Gerald D. Sharkin; Robert S. Honor; Timothy G. Rothwell

[57] ABSTRACT

Substituted and unsubstituted α-t-butyl-p-xylene-α,α'-diols, e.g., α-t-butyl-p-xylene-α,α'-diol, are prepared from the corresponding 4-pivaloyl-benzyl alcohols and are useful as hypolipidemic agents.

4 Claims, No Drawings

α-T-BUTYL-P-XYLENE-α-α'-DIOLS AND HYPOLIPIDEMIC COMPOSITIONS CONTAINING SAME

This invention relates to p-xylene-α,α'-diols, their method of preparation, and their use in pharmaceutical compositions.

The compounds of this invention may be represented by the following structural formula:

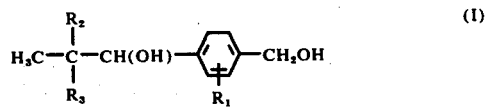

where
$R_1$ is hydrogen or halo having an atomic weight of about 19 to 80, i.e., fluoro, chloro, or bromo, and
$R_2$ and $R_3$ are each independently methyl or ethyl.

The compounds of formula (I) may be prepared according to the following reaction scheme:

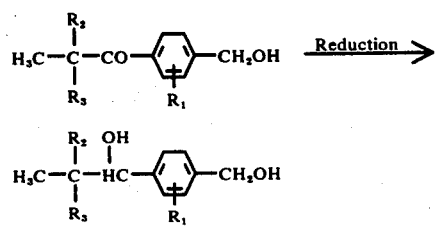

where
$R_1$, $R_2$, and $R_3$ are as defined above.

The compounds of formula (I) are prepared by reducing a compound of formula (II) with an organometallic reducing agent, for example, an alkali metal hydride, such as potassium aluminum hydride, lithium aluminum hydride or sodium borohydride, an organo aluminum hydride, e.g., diisobutyl aluminum hydride, triisobutyl aluminum hydride, and the like or sodium aluminum diethyl dihydride in the presence of an inert organic solvent. The alkali metal hydrides, in particular, lithium aluminum hydride are especially preferred. Although the particular solvent used is not critical, it is preferred that the reaction be carried out in the presence of an ether, such as tetrahydrofuran, diethylether, and the like, when an alkali metal hydride is used as the reducing agent or in the presence of a lower alkanol, such as methanol, ethanol, isopropanol, and the like, when sodium borohydride is used as the reducing agent. The temperature at which the reaction is carried out is not critical, but it is preferred that the reaction be carried out between about −10° C. to about 50° C., preferably from about 20° to 25° C. The reaction may be run from about 1 to 10 hours, preferably about 5 hours. The product is recovered using conventional techniques, e.g., recrystallization.

The compounds of formula (II) are prepared by the following reaction scheme:

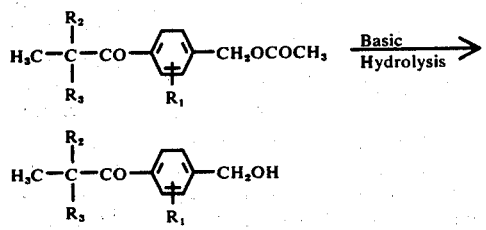

where $R_1$, $R_2$, and $R_3$ are as defined above.

The compounds of formula (II) are prepared by treating a compound of the formula (III) with a base in an aqueous solvent. The base used in the reaction can be any alkali metal base, such as sodium hydroxide, potassium hydroxide, and the like. The aqueous solvent used is not critical, but it is preferred that the reaction be carried out using a water-miscible lower alkanol, such as methanol, ethanol, isopropanol, and the like, especially ethanol. The temperature at which the reaction is carried out is not critical, but it is preferred that the reaction be run between 40° to 50° C., preferably between about 80° to 100° C. The time of the reaction also is not critical, but it is preferred that the reaction be run for 1 to 10 hours, for example, about 4 hours. The compound of formula (II) is recovered using conventional techniques, e.g., extraction and evaporation.

The compounds of formula (III) are prepared by the following reaction scheme:

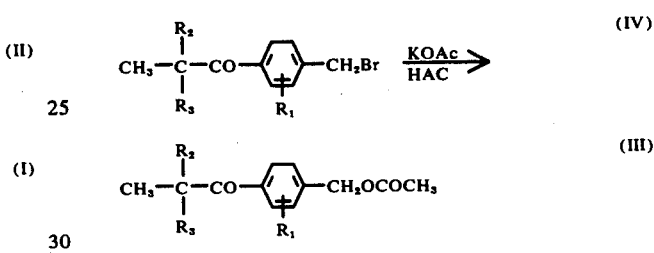

where $R_1$, $R_2$, and $R_3$ are as defined above.

The compounds of formula (III) are prepared by reacting a compound of formula (IV) with potassium acetate in acetic acid as the solvent. The temperature at which the reaction is carried out is not critical, but it is preferred that the reaction be carried out between about 60° to 150° C., preferably at the reflux temperature of the reaction medium. The time of the reaction also is not critical, but it is preferred that the reaction be run for about 12 hours to about 30 hours, for example, 20 hours. The compounds of formula (III) are recovered by conventional techniques, e.g., extraction and evaporation.

Many of the compounds of formula (IV) are known and may be prepared by methods described in the literature. Those compounds of formula (IV) not specifically disclosed may be prepared by analogous methods from known starting materials.

The compounds of formula (I) are useful because they possess pharmacological activity in animals. In particular, the compounds of formula (I) are useful as hypolipidemic agents in the treatment of lipidemia, in particular, hyperlipoproteinemia, as indicated by the fall in cholesterol and triglyceride levels in male albino Wistar rats weighing 110 to 130 g., initially. The rats are maintained on drug-free laboratory chow diet for 7 days and then divided into groups of 6 to 10 animals. Each group, with the exception of the control, is then given orally 30 to 250 milligrams per kilogram of body weight per diem of the test compound for 6 days. At the end of this period, the animals are anestheized with sodium hexobarbital and bled from the carotid arteries. Serum or plasma samples are collected and 1.0 ml. of the serum is added to 9.0 ml. redistilled isopropanol. Two autoanalyzer cupsful of a mixture of zeolite-copperhydroxide and Lloydds reagent (Kersler, G., and Lederer, H., 1965, Technicon Symposium, Madiad, Inc., New York, 345–347) are added and the mixture is shaken for 1 hour. Cholesterol and triglyceride levels are determined simultaneously on the same sample by Technicon N 24A (cholesterol) and N-78 (triglyceride) methodology. The mean total serum cholesterol levels are then computed and the hypocholesterol activity is expressed as the fall in cholesterol levels as a percentage of the control level. The change in serum triglyceride levels induced by the drug is computed as a percentage of the control triglyceride levels.

The compounds of formula (I) are further useful as anti-diabetic agents in the treatment of diabetes as indicated by the lowering of blood glucose in 6 to 8 week old male Royal Hart mice weighing 30 to 35 g. which are fasted in groups of 5 mice for 16 hours and then are given an initial dose of 200 milligrams per kilogram of animal body weight of the compound orally. Two hours after administration, the mice are anesthetized with 85 milligrams per kilogram of animal body weight of sodium hexobarbital after which blood is collected, via cardiac puncture. The blood samples are placed in an Auto Analyzer Cup containing 0.025 milliliters of heparin (1,000 units per milliliter); and the samples are capped, shaken, and stored in ice. The glucose content is determined by the Auto Analyzer potassium ferric-cyanide number N-2b method and are compared with a control group, which receive orally 0.5 percent carboxymethylcellulose vehicle and are run concurrently.

For such uses, the compounds of formula (I) may be administered orally or parenterally as such or admixed with conventional pharmaceutical carriers. They may be administered orally in such forms as tablets, dispersible powders, granules, capsules, syrups, and elixirs, and parenterally as solutions, e.g., a sterile injectable aqueous solution. The injectable compositions are formulated as known in the art. These pharmaceutical preparations may contain up to about 90 percent of the active ingredient in combination with the carrier or adjuvant.

The hypolipidemic effective dosage of active ingredient employed for the treatment of lipidemia may vary depending on the particular compound employed, the mode of administration and the severity of the condition being treated. However, in general, satisfactory results are obtained when the compounds of formula (I) are administered at a daily dosage of from about 4 milligrams to about 250 milligrams per kilogram of animal body weight, p.o., preferably given in divided doses 2 to 4 times a day, or in sustained release form. For most larger mammals, the total daily dosage is from about 300 to about 2,000 milligrams. Dosage forms suitable for internal use comprise from about 75 to about 1,000 milligrams of the active compound in intimate admixture with a solid or liquid pharmaceutically acceptable carrier or diluent.

The anti-diabetic effective dosage of active ingredient employed for the treatment of diabetes may vary depending on the particular compound employed, the mode of administration, and the severity of the condition being treated. However, in general, satisfactory results are obtained for the antidiabetic effect when the compounds of formula (I) are administered at a daily dosage of from about 10 milligrams to about 200 milligrams per kilogram of animal body weight, p.o., preferably given in divided doses two to four times a day, or in sustained release form. For most large mammals, the total daily dosage is from about 750 to about 3,000 milligrams. Dosage forms suitable for internal use comprise from about 185.5 to 1500 milligrams of the active compound in intimate admixture with a solid or liquid pharmaceutically acceptable carrier of diluent.

A representative formulation suitable for oral administration is a tablet or capsule prepared by standard tabletting or encapsulating techniques which contains the following and may be administered 2 to 4 times a day in the treatment of lipidemia or diabetes:

| Ingredient | Weight (mg.) tablet | capsule |
|---|---|---|
| α-t-butyl-p-xylene-α,α'-diol | 200 | 200 |
| tragacanth | 10 | — |
| lactose | 247.5 | 300 |
| corn starch | 25 | |
| talcum | 15 | |
| magnesium stearate | 2.5 | |
| TOTAL | 500 mg. | 500 mg. |

EXAMPLE 1

α-t-butyl-p-xylene-α,α'-diol

Step 1--α-acetoxy-p-pivaloyl-toluene

A mixture of 20.0 grams (0.0785 mole) of α-bromo-p-pivaloyl-toluene, 30.0 grams (0.157 mole) of potassium acetate and 60 milliliters of glacial acetic acid is refluxed for 20 hours. The acetic acid is removed in vacuo, and the residue is treated with ice water and then extracted with methylene chloride. The methylene chloride extract is washed with 2N sodium hydroxide solution, dried with magnesium sulfate, and then filtered and evaporated to give α-acetoxy-p-pivaloyl-tolune.

Following the above procedure, but using α-bromo-2-chloro-4-pivaloyl-toluene in place of the α-bromo-p-pivaloyl-toluene, there is obtained α-acetoxy-2-chloro-4-pivaloyl-toluene.

Step 2--p-pivaloyl-benzyl alcohol

A mixture of 15 grams (0.064 mole) of α-acetoxy-p-pivaloyl-toluene and 15 grams (0.278 mole) of potassium hydroxide in 150 milliliter of ethanol and 50 milliliters of water is refluxed for 4 hours. The solvent is removed in vacuo, and the residue is treated with ether and water. The ether is separated and the water is again extracted with ether. The ether layers are combined, decolorized with charcoal, dried over magnesium sulfate, filtered and evaporated. The resulting yellow oil is distilled in vacuo to give p-pivaloyl benzyl alcohol (b.p. 100° to 105° C./0.1 milliliters).

Following the above procedure, but using an equivalent amount of α-acetoxy-2-chloro-4-pivaloyl-toluene in place of the α-acetoxy-p-pivaloyl-toluene, there is obtained 2-chloro-4-pivaloyl-benzyl alcohol.

Step 3--α-t-butyl-p-xylene-α,α'-diol

A suspension of 2.7 grams (0.070 mole) of lithium aluminum hydride in 170 milliliters of dry tetrahydrofuran is cooled to 0° and treated by dropwise addition with 6.7 grams (0.035 mole) of p-pivaloyl benzyl alcohol in 70 milliliters of dry tetrahydrofuran. The resulting mixture is stirred for 5 hours at room temperature, and then cooled to 0° C. and treated by dropwise addition with saturated sodium sulfate solution. The mixture is filtered and the filter cake is washed thoroughly with tetrahydrofuran. The tetrahydrofuran is dried over magnesium sulfate, filtered and evaporated to give α-t-butyl-p-xylene-α,α'-diol, m.p. 91° to 95° C.

Following the above procedure, but using an equivalent amount of 2-chloro-4-pivaloyl-benzyl alcohol in place of the p-pivaloyl benzyl alcohol, there is obtained 2-chloro-4-(2,2-dimethyl-1-hydroxypropyl)-benzyl alcohol.

What is claimed is:
1. A compound of the formula:

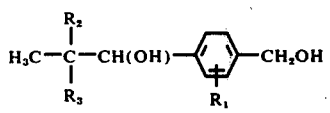

where
R₁ is hydrogen or halo having an atomic weight of about 19 to 80 and
R₂ and R₃ are each independently methyl or ethyl.
2. The compound according to claim 1, which is α-t-butyl-p-xylene-α,α'-diol.
3. The compounds of claim 1 in which R₂ and R₃ are both methyl.
4. A hypolipidemic composition comprising as the active ingredient a hypolipidemic amount of a compound according to claim 1 in combination with a pharmaceutically acceptable carrier or excipient.

* * * * *